United States Patent [19]

Meserve

[11] Plant 4,685

[45] Apr. 7, 1981

[54] ILEX PLANT - MESID VARIETY

[75] Inventor: Kathleen K. Meserve, St. James, N.Y.

[73] Assignee: The Conard-Pyle Company, West Grove, Pa.

[21] Appl. No.: 64,511

[22] Filed: Aug. 7, 1979

[51] Int. Cl.[3] ..... A01H 5/00

[52] U.S. Cl. ..... Plt./65

[58] Field of Search ..... Plt./65

*Primary Examiner*—Robert E. Bagwill

*Attorney, Agent, or Firm*—Burns, Doane, Swecker & Mathis

[57] ABSTRACT

A new and distinct variety of Ilex X meserveae produced by crossing an *Ilex aquifolium* seeding X *Ilex rugosa* seeding is provided. The new variety of Blue Holly is a female which bears unusually large foliage and exhibits superior cold tolerance.

No Drawings

SUMMARY OF THE INVENTION

The present invention relates to a new and distinct variety of Ilex X meserveae which was originated by me by crossing an *Ilex aquifolium* seedling X *Ilex rugosa* seedling.

The objective of my breeding was to create an improved and more versatile decorative shrub of the genus Ilex, combining the attractiveness of *Ilex aquifolium* with a considerably greater tolerance to cold than *Ilex rugosa,* and especially well-suited to a wide range of environmental landscape needs in a wide range of climates. As a result of this breeding, I have attained my objective, along with other improvements, and produced a new, distinct, and improved Ilex which is distinguished from its parents and all other Ilex of which I am aware, as evidenced by the following unique combination of characteristics:

(a) an attractive, vigorous, densely branched upright evergreen shrub, (b) deep green leaves with good luster on the upper surface which are longer and wider than the leaves of previously patented female varieties of Ilex X meserveae, such as Blue Girl (U.S. Plant Pat. No. 2,434), Blue Angel (U.S. Plant Pat. No. 3,662) and Blue Princess (U.S. Plant Pat. No. 3,675), (c) pistillate flowers commonly borne abundantly in May and in lesser quantities from June through October, (d) fruit set occurring more or less continuously from each flowering with the berries maturing to a vibrant red in the order of flowering, and (e) superior cold tolerance compared to Ilex X meserveae Blue Girl (U.S. Plant Pat. No. 2,434), Blue Boy (U.S. Plant Pat. No. 2,435), Blue Prince (U.S. Plant Pat. No. 3,517), Blue Angel (U.S. Plant Pat. No. 3,662), and Blue Princess (U.S. Plant Pat. No. 3,675).

The present variety is one of the most vigorous varieties of Ilex x meserveae to be introduced to date. For instance, two year old container grown plants of the present variety are at least as vigorous as those of the Blue Princess variety (U.S. Plant Pat. No. 3,675) and measure approximately 15 to 18 inches in height and breadth. For comparative purposes two year old container grown plants of the Blue Angel variety (U.S. Plant Pat. No. 3,662) measure approximately 10 to 12 inches in height and breadth.

This cold tolerance is considerably superior to *Ilex opaca* which is listed as hardy to only Zone 6, and *Ilex aquifolium,* which is listed as hardy to only Zone 7 (Plant Hardiness Zone Map, Miscellaneous Publication No. 814 of USDA, Revised 1965). Similarly root hardiness is superior to *Ilex crenata compacta,* Ilex X "Nellie Stevens," Ilex X "Dr. Kassab," *Ilex crenata* "Helleri," *Ilex crenata* "Hetzi," *Ilex crenata* "National," *Ilex crenata* "Compacta," *Ilex crenata* "Buxifolia," *Ilex opaca* "New Jersey Special," Ilex X "Lydia Morris," Ilex X "Edward T. Stevens," Ilex X "John Morris," Ilex cornuta "National," *Ilex aquifolium* "New York Botanic Garden #2," all of which were killed, except "New York Botanic #2," which was seriously injured but not killed, when overwintered in containers above ground at West Grove, Pa., while my present variety survived without injury. The present variety has successfully withstood in the absence of defoliation or other damage winter temperatures of 0° C. while grown above ground in containers.

Asexual reproduction of my new variety by cuttings has been accomplished at St. James, N.Y. and at West Grove, Pa. It has been demonstrated that the unique combination of characteristics has been established and transmitted to successive generations.

The new variety has been named the Mesid variety.

BRIEF DESCRIPTION OF THE PHOTOGRAPH

The accompanying photograph shows typical specimens of my new variety, some with flowers, as depicted in color as true as reasonably possible to make the same in a color illustration of this character. The plant illustrated was grown at West Grove, Pa.

DETAILED DESCRIPTION

The following is a detailed description of my new variety, with color terminology in accordance with the R.H.S. Colour Chart of the Royal Horticultural Society, London, England. The description was obtained following the observation of seven year old plants growing at West Grove, Pa.

Type: Hardy outdoor evergreen shrub for garden decoration and general landscape use.

Parentage: *Ilex aquifolium* seedling X *Ilex rugosa.*

Class: Ilex X meserveae.

Propagation: It does hold its distinguishing characteristics through succeeding propagations by cuttings.

Flowers: Pistillate flowers are borne several to the stem, in regular rounded clusters, on normal medium stems. Flowers are borne freely outdoors.

*Bud.*—Flowers are carried on a short-medium length, medium diameter, stiff peduncle, light green, of the Yellow-Green Group 146D. Peduncle is smooth. Before the calyx breaks, the size is small, buds are short globular without foliaceous appendages on the surface of the bud, or extending beyond the tip of the bud. As the calyx breaks the color is of the Red Group 54C. As the first petal opens, the buds are small, globular with color of the Red Group 56D on the outside and inside.

*Bloom.*—Blooms are small in size—approximately 6 mm. in diameter. Petalage is single—4 petals joined in the center. Form is cupped and globular at first, becoming flat; petals remaining at first loosely cupped inward; becoming later at maturity loosely flat inward. Petals are thin and soft, and satiny on inside and outside.

*Color.*—Outside surface: Red Group 56D shaded with Red Group 54C. Inside Surface: Red Group 56D shaded with Red Group 54D. Petals drop off cleanly. Flowers last on the bush in the outdoor garden approximately 1 to 2 days in May.

*Reproductive organs.*—Pistils: 4. Styles: Even, long, medium separated. Stigma: White. Ovaries: All protruding from receptacle. Fruit: Round, approximately 9–11 mm. in diameter.

Foliage:

*Leaves.*—Elliptic, with apex acuminate and base obtuse. Leaf margins are serrate.

*Leaf size.*—Measurements taken from a random sampling of mature current year's growth growing midway along the main stems (measurements to tips of spines): width approximately 3.5 to 4.25 cm.; length approximately 5.3 to 6.0 cm. Lateral branches on current year's growth: width approximately 2.1 to 3.1 cm.; length approximately 3.4 to 4.6 cm.

*Petiole.*—Approximately 3 to 7 mm.

*Spines.*—Approximately 14 to 19 on leaves growing midway along main stem of current year's growth; approximately 8 to 16 on lateral branches on current year's growth.

*Color of mature leaves in winter.*—Upper Surface—Very glossy, Green Group 139A. Under Surface—Dull, Yellow-Green Group 146B. Older Leaf—Upper surface, Green Group 139A. Under surface, Yellow-Green Group 146A. Young stems: Current year's growth, Purple Group 79. Mature stems: 2 to 3 year's old, Green Group 143A.

*Color of foliage in May.*—Young foliage: Upper surface, Green Group 137B. Under surface, Yellow-Green Group 144B. Previous year's growth: Upper surface, very glossy, Yellow-Green Group 147A. Under surface, dull, Yellow-Green Group 144A.

*Berries.*—Mature color: Red Group 43A, bright and glossy. Mature size: Obviously larger than Blue Girl (U.S. Plant Pat. No. 2,434), and Blue Princess (U.S. Plant Pat. No. 3,675); approximately 9 to 11 mm. in diameter.

I claim:

1. A new and distinct variety of Ilex X meserveae plant, substantially as herein shown and described, characterized particularly as to novelty by the unique combination of:

(a) a vigorous, densely branched upright evergreen shrub,
(b) deep green foliage of unusually large size,
(c) pistillate flowers borne abundantly in May,
(d) berries which mature to a vibrant red color, and
(e) a superior cold tolerance.

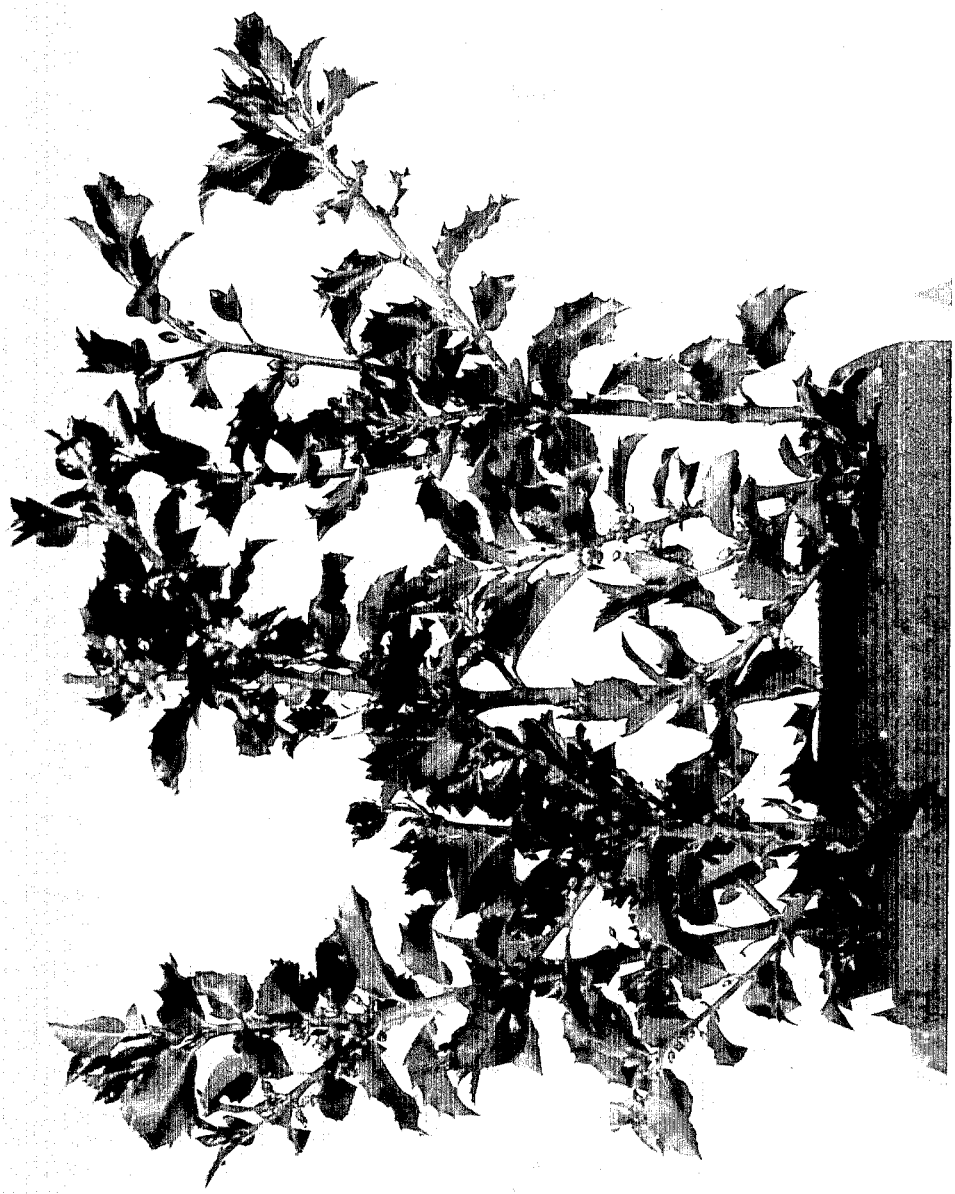

* * * * *